US006929793B2

(12) United States Patent
Spivey-Krobath et al.

(10) Patent No.: US 6,929,793 B2
(45) Date of Patent: Aug. 16, 2005

(54) NUTRITIONAL COMPOSITION FOR TREATING AN IMMUNE CONDITION

(75) Inventors: Evelyn Spivey-Krobath, Savigny (CH); Claude Cavadini, Mont-Sur-Rolle VD (CH); Ferdinand Haschke, Grünwald (DE); Veronique Jaussan, Vincennes (FR); Eduardo Schiffrin, Crissier (CH)

(73) Assignee: Nestec S.A., Vevey (CH)

( * ) Notice: Subject to any disclaimer, the term of this patent is extended or adjusted under 35 U.S.C. 154(b) by 82 days.

(21) Appl. No.: 10/436,477

(22) Filed: May 13, 2003

(65) Prior Publication Data

US 2004/0005305 A1 Jan. 8, 2004

Related U.S. Application Data

(63) Continuation of application No. PCT/EP01/13302, filed on Nov. 14, 2001.

(30) Foreign Application Priority Data

Nov. 14, 2000 (GB) ............................................. 0027761

(51) Int. Cl.$^7$ ........................... A23C 9/12; A61K 47/00; A01N 63/00; C12N 1/12; C12N 1/20
(52) U.S. Cl. ....................... 424/93.4; 424/439; 426/61; 435/170; 435/252.1
(58) Field of Search ................................ 424/93.4, 439, 424/93.1; 426/61; 435/170, 252.9, 41

(56) References Cited

U.S. PATENT DOCUMENTS

| | | | | |
|---|---|---|---|---|
| 5,147,668 | A | 9/1992 | Munk ........................... | 426/61 |
| 5,185,321 | A | 2/1993 | Link et al. ..................... | 514/8 |
| 5,882,704 | A | 3/1999 | Yamaguchi et al. .......... | 426/36 |
| 6,241,983 | B1 * | 6/2001 | Paul et al. .................. | 424/93.4 |

FOREIGN PATENT DOCUMENTS

| | | |
|---|---|---|
| EP | 0741995 | 11/1996 |
| EP | 0 904 784 A1 | 3/1999 |
| EP | 0966969 | 12/1999 |
| GB | 2018124 | 10/1979 |

OTHER PUBLICATIONS

G. Schaafsma et al., "Effects of Milk Product, Fermented by *Lactobacillus acidophilus* and with Fructo–oligosaccharides Added, on Blood Lipids in Male Volunteers," European Journal of Clinical Nutrition, vol. 52 no. 6, pp. 436–440, Abstract XP002119336 p. 437. (Jun. 1998).

A. Sullivan et al., "Effect of *Lactobacillus paracasei* on intestinal colonisation of lactobacilli, bifidobacteria and clostridium difficile in elderly persons," Abstract XP002194824. (Apr. 2001).

R. Nemcova et al., "Study of the effect of *Lactobacillus paracasei* and fructooligosaccharides on the faecal microflora in weanling piglets," Abstract XP002194825. (Jun.–Jul. 1999).

E. Shiffrin et al., "Immune modulation of blood leukocytes in humans by lactic acid bacteria: criteria for strain selection," American Journal of Clinical Nutrition, vol. 66, pp. 515s–520s. Abstract XP002194826. (1997).

P. Marteau et al., "Effects of intrajejunal perfusion and chronic ingestion of *Lactobacillus johnsonii* strain La1 on serum concentrations and jejunal secretions of immunoglobulins and serum proteins in healthy humans," Gastroenterol. Clin. Biol., vol. 21, pp. 293–298. Abstract XP001062975. (1997).

J. Spiegel et al., "Safety and Benefits of Fructooligosaccharides as Food Ingredients," Food Technology, vol. 48, no. 1, pp. 85–89. Abstract XP 000423511. (Jan. 1994).

M. E. Sanders, "Probiotics," Food Technology, vol. 53, no. 11, pp. 67–75. (Nov. 1999).

C. L. Riedel Abstract of German Patent DD154424; Abstract No. 1982–70334E.

* cited by examiner

*Primary Examiner*—David M. Naff
*Assistant Examiner*—Deborah K. Ware
(74) *Attorney, Agent, or Firm*—Bell, Boyd & Lloyd LLC

(57) ABSTRACT

A nutritional composition is described for prevention or treatment of an immune condition. The composition includes at least vitamin E, vitamin C, vitamin B6, folic acid, vitamin B12, copper, zinc, selenium, fructo-oligosaccharides and/or gum acacia, a probiotic lactic acid bacterium. For example, in an embodiment it comprises per 300 g: 150 IU Vitamin E, 120 mg Vitamin C, 2 mg Vitamin B6, 400 ug Folic acid, 3.8 ug Vitamin B12, 1.5 mg Copper, 15 mg Zinc, 100 ug Selenium, 3 g Fructo-oligosaccharides and/or gum acacia, 10E10 cfu ST11 lactobacillus. Also disclosed are a method for making the nutritional composition, a method for manufacturing a functional food or medicament; and a method of prevention or treatment of an immune condition by administering an effective amount of the composition, functional food or medicament.

20 Claims, No Drawings

NUTRITIONAL COMPOSITION FOR TREATING AN IMMUNE CONDITION

CROSS-REFERENCE TO RELATED APPLICATION

This application is a continuation of the US national phase of International application PCT/EP01/13302 filed Nov. 14, 2001, the content of which is expressly incorporated herein by reference thereto.

BACKGROUND ART

The present invention relates to a nutritional composition for prevention or treatment of an immune condition, a method of production of the composition, use of the composition in the manufacture of a functional food or medicament for the prevention or treatment of an immune condition and a method of treatment of an immune condition which comprises administering an effective amount of the composition.

At the turn of the century, Americans older than 65 years old accounted for 4% of the US population. Currently, they account for greater than 12% of the population. However, although they only account for 12% of the US population, they account for greater than 40% of acute hospital bed days, buy greater than 30% of all prescription drugs and spend 30% of the US health budget. Furthermore, it has been estimated that in 2030, greater than 70 million Americans (1:5) will be over the age of 65, and those over 85 are expected to experience the highest percentage increase of all age groups.

As the average age of the population increases, obtaining a better understanding of the unique aspects of aging in relation to nutritional needs and treatment is imperative. Many physiologic functions decline progressively throughout adult life and have an impact on nutrition. For instance, a reduction in the number of functioning cells and the resultant slowing of metabolic processes results in a decrease in caloric requirements among the elderly. Also, the reduction in physical activity that generally accompanies aging further decreases energy requirements.

Merely decreasing the total caloric intake of an elderly patient may adversely affect their required nutrition. When the total caloric intake is reduced, the remaining food intake must carefully insure a properly balanced intake of proteins, vitamins and minerals. To reduce caloric intake in the elderly, consumption of "empty" calories (i.e. fats) can be reduced and consumption of nutrient-dense foods (i.e. carbohydrates and proteins) can be increased.

While the nutritional needs of the mature adult differ from those of an adult, in health care settings, standard nutritional formulae are the primary form of elemental nutrition currently used. Naturally, standard formulae do not take into account the nutritional needs of an elderly patient. Standard products suffer from the problem that they must be supplemented with key micronutrients to compensate for common deficiencies and metabolic changes of an elderly patient. Therefore, a need exists for a nutritional composition which meets the nutritional needs of an elderly patient.

In addition to the above problems, a composition is required to address the problems of immune conditions in the elderly as well as in clinical and performance settings, for example, with regard to an athlete recovering from injury.

Furthermore, it is known that the effects of diet and nutritional supplements can play a role in improving the survival and quality of life. In particular, a need exists for a nutritional composition which can help to improve health, in particular with regard to an immune condition.

Furthermore, it is known that the problem of an impaired immune response can be associated with aging, chronic pathological conditions and/or malnutrition. This problem has been partly addressed by providing nutritional supplements. However, these supplements suffer from the problem that, generally, they are specific for certain ailments and do not provide good nutritional support for patients suffering from a more complicated combination of conditions. This is particularly relevant with respect to an elderly patient. In addition, the increase in the likelihood of chronic disease such as arthritis, gastritis, etc, with age leads to an increase in inflammatory reactions.

Furthermore, a need exists for a nutritional composition which addresses the problems associated with infectious diarrhea (rotavirus and bacterial infection), allergy, restoration of and maintenance of gut integrity, bacterial overgrowth, endotoxemia and gut permeability.

SUMMARY OF THE INVENTION

The present invention addresses and resolves the problems set forth in the previous section. Remarkably, a composition has now been found that can be used to provide general nutrition to an elderly patient, as well as performance nutrition, e.g., to an athlete, or clinical nutrition to a hospital patient.

To accomplish this, the present invention provides a composition comprising a new combination of ingredients, including a source of protein, a source of carbohydrate, a source of fat, a probiotic lactic acid bacterium, fructo-oligosaccharides and/or gum acacia. The probiotic lactic acid bacterium is advantageously present in an amount sufficient to help treat an immune condition of a subject who consumes the composition.

The invention also provides a method of producing the composition by blending the required nutrients together in the required amounts to form the composition.

In addition, the invention provides a method of manufacturing a functional food or a medicament for the prevention or treatment of an immune condition by incorporating or including these compositions in the food or medicament.

The invention also provides a method of prevention or treatment of an immune condition which comprises administering to a subject in need of such treatment an effective amount of one of the compositions, foods or medicaments described herein.

DETAILED DESCRIPTION OF PREFERRED EMBODIMENT

Within the context of this specification the word "comprises" is taken to mean "includes, among other things". It is not intended to be construed as "consists of" or "only".

Within the context of this specification the term "an immune condition" represents an ailment selected from the group which comprises an impaired immune response, an inflammatory condition, inflammation, chronic disease (for example arthritis or gastritis), conditions associated with aging and leading to an increase of inflammatory responses.

The present invention provides a composition which comprises a source of protein, a source of carbohydrate, a source of fat, a probiotic lactic acid bacterium, fructo-oligosaccharides and/or gum acacia.

The one or more probiotic lactic acid bacteria are selected from the group consisting of paracasei and johnsonii bacteria. More preferably, an embodiment of a composition according to the invention comprises one or more probiotic lactic acid bacteria selected from the group which consists of ST11 (deposited under the number NCCMI-2116) and La1 (deposited under the number NCCMI-1225).

Advantages in treating immune conditions provided by the probiotic bacteria include prevention or inhibition of diarrhea brought about by pathogenic bacteria; prevention or inhibition of diarrhea, especially infections of intestinal cells by rotavirus; prevention of colonization of the intestine by pathogenic bacteria causing diarrhea; and an ability to adhere to and colonize the intestinal mucosa of a host organism.

Preferably, one or more nutrients or minerals selected from the group consisting of vitamin E, vitamin C, vitamin B6, folic acid, vitamin B12, copper, zinc and selenium are included in the composition. More preferably, at least two of these nutrients or minerals are included. Even more preferably, at least three of these nutrients or minerals are present. Most preferably it includes all of these minerals or nutrients.

Another embodiment of the invention additionally comprises one or more nutrients or minerals selected from the group consisting of calcium, phosphorus, magnesium, iron, vitamin A, vitamin B1, vitamin B2, niacin and vitamin D. More preferably, it comprises at least two of these nutrients or minerals. Even more preferably, it comprises at least three of these nutrients or minerals. Most preferably all of these minerals or nutrients are present.

These compositions preferably include gum acacia. It is also desirable to include calcium in the form of milk calcium or calcium derived from milk calcium in the composition, preferably with the nutrients described previously.

Preferably, the following masses or amounts of nutrients or minerals (if present) are included per 300 g of the composition. Preferably, this is the amount of composition administered per day:

Vitamin E: preferably about 1 IU to about 400 IU, most preferably about 120 mg

Vitamin C: preferably about 6 mg to about 300 mg, most preferably about 120 mg

Vitamin B6: preferably about 0.17 mg to about 3 mg, most preferably about 2 mg

Folic acid: preferably about 40 µg to about 800 µg, most preferably about 400 µg Vitamin B12: preferably about 0.24 µg to about 5 µg, most preferably about 3.8 µg Copper: preferably about 0.3 mg to about 3 mg, most preferably about 1.5 mg Zinc: preferably about 1.5 mg to about 15 mg, most preferably about 15 mg Selenium: preferably about 7 µg to about 300 µg, most preferably about 100 µg Fructo-oligosaccharides and/or gum acacia: preferably about 4 g to about 50 g, most preferably about 6 g Lactic acid bacteria: preferably about 10E8 to about 10E12 cfu, most preferably about 10E10 cfu.

Preferably, the invention further comprises one or more nutrients selected from the following masses or amounts of nutrients or minerals (if present) per 300 g of the composition. Again, this is the amount of composition administered per day:

calcium: about 100 mg to about 300 mg, more preferably about 200 mg;

phosphorus: about 50 mg to about 615 mg, more preferably about 150 mg;

magnesium: about 110 mg to about 210 mg, more preferably about 60 mg;

vitamin A: about 1000 IU to about 1500 IU, more preferably about 1333 IU;

vitamin D: about 50 IU to about 150 IU, more preferably about 100 IU;

vitamin E: about 5.0 IU to about 150 IU, more preferably about 120 IU;

vitamin C: about 30 mg to about 500 mg, more preferably about 120 mg;

vitamin B1: about 0.1 mg to about 2 mg, more preferably about 0.25 mg;

vitamin B2: about 0.1 mg to about 0.6 mg, more preferably about 0.3 mg;

niacin: about 1.5 mg to about 7.2 mg, more preferably about 3 mg;

vitamin B6: about 1.0 mg to about 3.0 mg, more preferably about 2 mg;

folic acid: about 200 µg to about 600 µg, more preferably about 400 µg;

vitamin B12: about 1.5 µg to about 4.5 µg, more preferably about 3.8 µg;

iron: about 2.0 mg to about 5 mg, more preferably about 2.75 mg; and zinc: about 10 mg to about 20 mg, more preferably about 15 mg.

An advantage of the present invention is that it provides a nutritional composition in the form of a powder or dry granulate that can be dissolved instantaneously in water to provide a beverage or soup. It does not require cooking.

Another advantage of the present invention is that it provides a single composition that can be adapted and administered simply in a food for the prevention or treatment an immune condition. The composition can be provided in clinical or performance nutrition settings and is particularly suitable for an elderly patient.

Yet another advantage of the present invention is that it provides a composition beneficial for diabetics. This is due to the specific composition of macronutrients, protein, carbohydrate and fat which provides a low glycemic index.

Additional features and advantages of the present invention are described in, and will be apparent from the description of the presently preferred embodiments which are set out below.

For the purposes of clarity and a concise description features are described herein as part of the same or separate embodiments, however it will be appreciated that the scope of the invention may include embodiments having combinations of all or some of the features described.

In an embodiment, a nutritional composition comprises a source of protein. The protein source preferably provides about 5% to about 55% of the energy of the nutritional formula; for example about 20% to about 50%, preferably 26%, of the energy. Dietary protein is preferred as a source of protein. The dietary protein may be any suitable dietary protein; for example animal protein (such as milk protein, meat protein or egg protein); vegetable protein (such as soy protein, wheat protein, rice protein, and pea protein); a mixture of free amino acids; or a combination thereof. Milk proteins such as casein, whey proteins and soy proteins are particularly preferred.

The composition also comprises a source of carbohydrates and a source of fat. A fat source preferably provides about 5% to about 55% of the energy of the nutritional formula; for example about 20% to about 50%, preferably 23%, of the energy. Lipid making up the fat source may be any suitable fat or fat mixture. Vegetable fat is particularly suitable; for example soy oil, palm oil, coconut oil, safflower oil, sunflower oil, corn oil, canola oil, lecithins, and the like. Most preferably it is a mixture of canola and soy oils. Animal fat such as milk fat may also be added if desired.

Preferably the composition comprises saturated fat which preferably comprises about 1% to about 5%, more preferably 2.5% of the total energy of the product. Preferably it comprises monounsaturated fat which preferably comprises about 5% to about 15%, more preferably 9.9% of the total energy of the product. Preferably the composition comprises polyunsaturated fat which preferably comprises about 5% to about 15%, more preferably 10.1% of the total energy of the product. Preferably the composition comprises linoleic acid which preferably comprises about 5% to about 15%, more preferably 8.5% of the total energy of the product. Preferably the composition comprises linoleic acid which preferably comprises about 0.5% to about 5%, more preferably 1.6% of the total energy of the product. Preferably the ratio of linoleic acid to linoleic acid is about 3 to about 8, more preferably about 5.3.

A source of carbohydrate preferably provides about 40% to about 80%, more preferably about 51% of the energy of the nutritional composition. Any suitable carbohydrate may be used, for example sucrose, lactose, glucose, fructose, corn syrup solids, maltodextrin, or a mixture thereof.

This embodiment of the composition additionally comprises about 10E10 cfu of paracaseii or johnsonii probiotic lactic acid bacteria and about 6 g of fructooligosaccharide and gum acacia per 300 g of the composition.

Dietary fiber may also be added. Preferably dietary fiber is present to provide up to about 5% of the energy of the nutritional composition. The dietary fiber may be from any suitable origin, preferably fructooligosaccharide, acacia gum, or a mixture thereof.

Additional suitable vitamins and minerals are included in the composition as described previously. Also, monosodium glutamate may be added as a flavor enhancer.

The nutritional composition is preferably enterally administrable; for example in the form of a powder, a liquid concentrate, or a ready-to-drink beverage. If it is desired to produce a powdered nutritional formula, the homogenized mixture is transferred to a suitable drying apparatus such as a spray drier or freeze drier and converted to powder.

Alternatively, a usual food product may be enriched with an embodiment of composition. For example, a fermented milk, a yogurt, a fresh cheese, a renneted milk, an article of confectionery, for example a sweet or sweetened beverage, a confectionery bar, breakfast cereal flakes or bars, a drink, milk powder, soy-based product, non-milk fermented product or a nutritional supplement for clinical nutrition. Then, the amount of the composition added is preferably at least about 0.01% by weight.

Preferably, an embodiment of a method according to the invention comprises the steps of blending the nutrients in the required amounts and extruding the blended mixture. More preferably it includes spray drying the mixture.

EXAMPLES

The following examples are given by way of illustration only and in no way should be construed as limiting the subject matter of the present application. Percentages and parts are by weight unless otherwise indicated.

Examples 1 and 2

Nutritional Compositions

Two nutritional compositions were made by blending the required constituents. Their compositions are indicated below in table 1. The compositions are intended to be consumed in the form of two oral supplements per day based on enriched beverages or milk product desserts. The total daily dose is intended to be approximately 300 g or 300 ml of composition.

TABLE I

| | Daily dose 300 ml/day | Daily dose 300 ml/day |
|---|---|---|
| Energy | 480 kcal (1.6 kcal/ml) | 300 kcal (1.0 kcal/ml) |
| P/L/C % TEI | 26%/24%/51% | 28%/30%/42% |
| Protein g/100 ml | 10.5 (with 6.25 g soy protein) | 7.0 |
| Fat g/100 ml | 4.16 | 3.3 |
| Carbohydrate g/100 ml | 20.6 | 10.5 |
| in daily dose | per 300 ml | per 300 ml |
| Na mg | 188 | 188 |
| K mg | 350 | 350 |
| Cl mg | 290 | 290 |
| Ca mg | 200 | 200 |
| P mg | 150 | 150 |
| Ca/P ratio | 1.3 | 1.3 |
| Mg mg | 60 | 60 |
| Mn $\mu$g | 495 | 495 |
| A IU | 1333 | 1333 |
| D IU | 100 | 100 |
| E IU | 120 | 150 |
| K1 $\mu$g | 13.8 | 13.8 |
| C mg | 120 | 120 |
| B1 mg | 0.25 | 0.25 |
| B2 mg | 0.3 | 0.3 |
| Niacin mg | 3 | 3 |
| B6 mg | 2.0 | 2.0 |
| Folic acid $\mu$g | 400 | 600 |
| Panto mg | 1.00 | 1.00 |
| B12 $\mu$g | 3.8 | 10.0 |
| Biotin $\mu$g | 7.5 | 7.5 |
| Fe mg | 2.75 | 2.75 |
| I $\mu$g | 75 | 75 |
| Cu mg | 1.5 | 1.5 |
| Zn mg | 15 | 6 |
| Se mg | 100 | 100 |
| Cr $\mu$g | 12.5 | 12.5 |
| Mo $\mu$g | 18.75 | 18.75 |
| Inulin & FOS blend (30:70 blend) g | 6 | 6 |
| Lactobacillus cfu/serving | Paracaseii $10^{10}$ | Johnsonii $10^{10}$ |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that all such changes and modifications be covered by the appended claims.

What is claimed is:

1. A nutritional composition comprising a source of protein, a source of carbohydrate, a source of fat, a probiotic lactic acid bacterium selected from the group consisting of NCCMI-2116 and NCCMI-1225, and additionally, a fructo-oligosaccharide or inulin, wherein the protein, carbohydrate and fat sources provide energy to a subject who consumes the composition, with the protein source providing about 5% to 55% of the energy, the carbohydrates source providing about 40% to 80% of the energy and the fat source providing about 5% to 55% of the energy, wherein the total amount of the energy provided by the protein, carbohydrate and fat sources is 100%, and the probiotic lactic acid bacterium is present in an amount sufficient to help treat an immune condition of the subject.

2. The composition of claim 1, wherein both a fructo-oligosaccharide and inulin are present and the probiotic lactic acid bacterium comprises one or more probiotic lactic acid bacterium selected from the group consisting of paracasei and johnsonii bacteria, and is present in an amount of about $10^8$ to $10^{12}$ cfu.

3. The composition of claim 1 which further comprises one or more of gum acacia, dietary fiber, a flavor enhancer, nutrients or minerals.

4. The composition of claim 3 wherein nutrients or minerals selected from the group consisting of vitamin E, vitamin C, vitamin B6, folic acid, vitamin B12, copper, zinc and selenium are present in the composition.

5. The composition of claim 4 wherein at least three of the recited nutrients or minerals are present in the composition.

6. The composition of claim 4 wherein one or more nutrients or minerals selected from the group consisting of calcium, phosphorus, magnesium, iron, vitamin A, vitamin B1, vitamin B2, niacin and vitamin D are also present in the composition.

7. The composition of claim 6 wherein at least three of the recited nutrients or minerals are present in the composition.

8. The composition of claim 1 which contains the fructo-oligosaccharide and gum acacia.

9. The composition of claim 1 wherein calcium, phosphorus, magnesium, iron, vitamin A, vitamin B1, vitamin B2, niacin and vitamin D are present in the composition.

10. The composition of claim 8 wherein the calcium is in the form of milk calcium or calcium derived from milk calcium.

11. The composition of claim 3 wherein the nutrients or minerals, are included in the following masses or amounts per 300 g of the composition:

Vitamin E: about 1 IU to about 400 IU,
Vitamin C: about 6 mg to about 300 mg,
Vitamin B6: about 0.17 mg to about 3 mg,
Folic acid: about 40 μg to about 800 μg,
Vitamin B12: about 0.24 mg to about 5 mg,
Copper: about 0.3 mg to about 3 mg,
Zinc: about 1.5 mg to about 15 mg,
Selenium: about 7 μg to about 300 μg,
Fructo-oligosaccharides and/or gum acacia: about 4 g to about 50 g,
Lactic acid bacteria: about $10^8$ to about $10^{12}$ cfu.

12. The composition of claim 3 wherein the nutrients or minerals, are included in the following masses or amounts per 300 g of the composition:

calcium: about 100 mg to about 300 mg,
phosphorus: about 50 mg to about 615 mg,
magnesium: about 110 mg to about 210 mg,
vitamin A: about 1000 IU to about 1500 IU,
vitamin D: about 50 IU to about 150 IU,
vitamin E: about 5.0 IU to about 150 IU,
vitamin C: about 30 mg to about 500 mg,
vitamin B1: about 0.1 mg to about 2 mg,
vitamin B2: about 0.1 mg to about 0.6 mg,
niacin: about 1.5 mg to about 7.2 mg,
vitamin B6: about 1.0 mg to about 3.0 mg,
folic acid: about 200 μg to about 600 μg,
vitamin B12: about 1.5 μg to about 4.5 μg,
iron: about 2.0 mg to about 5 mg,
zinc: about 10 mg to about 20 mg.

13. A method of producing the composition of claim 1 which comprises blending the required nutrients together in the required amounts to form the composition.

14. The method of claim 13 which further comprises extruding the blended mixture or spray drying the mixture to form a dry solid composition.

15. The composition produced by the method of claim 14.

16. A method of manufacturing a functional food or medicament for the prevention or treatment of an immune condition which comprises adding or incorporating an effective amount of the composition of claim 1 into a food or medicament to form the functional food or medicament.

17. The functional food or medicament produced by the method of claim 16.

18. A method of prevention or treatment of an immune condition which comprises administering the functional food or medicament of claim 17 to a subject in need of such treatment in an amount effective to treat such condition.

19. A method of prevention or treatment of an immune condition which comprises administering the composition of claim 15 to a subject in need of such treatment in amount effective to treat such condition.

20. A method of prevention or treatment of an immune condition which comprises administering the composition of claim 1 to a subject in need of such treatment in an amount to treat such condition.

* * * * *